(12) United States Patent
Hannon et al.

(10) Patent No.: US 11,701,489 B2
(45) Date of Patent: *Jul. 18, 2023

(54) CATHETER ASSEMBLY HAVING PROTECTIVE SLEEVE TIP

(71) Applicant: Hollister Incorporated, Libertyville, IL (US)

(72) Inventors: David Hannon, Ballina (IE); Seamus T. Kavanagh, Libertyville, IL (US); Jerome A. Henry, Castlebar (IE)

(73) Assignee: Hollister Incorporated, Libertyville, IL (US)

( * ) Notice: Subject to any disclaimer, the term of this patent is extended or adjusted under 35 U.S.C. 154(b) by 747 days.

This patent is subject to a terminal disclaimer.

(21) Appl. No.: 16/782,890

(22) Filed: Feb. 5, 2020

(65) Prior Publication Data

US 2020/0188631 A1   Jun. 18, 2020

Related U.S. Application Data

(63) Continuation of application No. 14/379,161, filed as application No. PCT/US2013/027781 on Feb. 26, 2013, now Pat. No. 10,646,688.

(Continued)

(51) Int. Cl.
*A61M 25/00* (2006.01)
*A61M 25/01* (2006.01)

(52) U.S. Cl.
CPC ...... *A61M 25/0017* (2013.01); *A61M 25/002* (2013.01); *A61M 25/0045* (2013.01);
(Continued)

(58) Field of Classification Search
CPC ............ A61M 25/0017; A61M 25/002; A61M 25/0045; A61M 25/0111;
(Continued)

(56) References Cited

U.S. PATENT DOCUMENTS 1,196,250 A   8/1916 Kuhn
1,351,917 A   9/1920 Kuhn
(Continued)

FOREIGN PATENT DOCUMENTS

DE            454642 A1   7/1928
DE         10031661 A1   1/2002
(Continued)

OTHER PUBLICATIONS

Notification of Transmittal of The International Search Report, International Search Report and Written Opinion for PCT/US2013/027781 dated Jun. 11, 2013.
(Continued)

*Primary Examiner* — Andrew J Mensh
(74) *Attorney, Agent, or Firm* — Cook Alex Ltd.

(57) ABSTRACT

A protective sleeve for a urinary catheter includes a sleeve configured to extend over an outer surface of the urinary catheter shaft from a proximal insertion end of the catheter shaft to a distal end of the catheter shaft. The protective sleeve includes a protective sleeve tip defining the proximal end portion of the sleeve. The sleeve and the protective sleeve tip are of a single unitary construction and the sleeve and protective sleeve tip are formed of the same thin, flexible film. The protective sleeve tips has a first pre-use configuration when a proximal insertion end of the catheter is not within the protective sleeve tip wherein the protective sleeve tip is in a collapsed state, and a second configuration when a proximal insertion end of a urinary catheter is inserted into the protective sleeve tip, in the second configuration the protective sleeve tip being in an extended state that is configured to cover the proximal insertion end of the urinary catheter shaft and the thin, flexible film conforms to and is supported by the proximal insertion end of the urinary
(Continued)

catheter for insertion of the protective sleeve tip into the urethral opening.

19 Claims, 11 Drawing Sheets

Related U.S. Application Data

(60) Provisional application No. 61/701,816, filed on Sep. 17, 2012, provisional application No. 61/603,577, filed on Feb. 27, 2012.

(52) U.S. Cl.
CPC . *A61M 25/0111* (2013.01); *A61M 2025/0046* (2013.01); *A61M 2025/0056* (2013.01); *A61M 2025/0062* (2013.01); *A61M 2025/0098* (2013.01); *A61M 2202/0496* (2013.01); *A61M 2210/14* (2013.01); *A61M 2210/16* (2013.01)

(58) Field of Classification Search
CPC .. A61M 2025/0046; A61M 2025/0056; A61M 2025/0062; A61M 2025/0098; A61M 2202/0496; A61M 2210/14; A61M 2210/16
USPC .......................................................... 604/544
See application file for complete search history.

(56) References Cited

U.S. PATENT DOCUMENTS

| | | | |
|---|---|---|---|
| 3,050,060 A | 8/1962 | Hoffman | |
| 3,084,693 A | 4/1963 | Cathcart | |
| 3,168,092 A | 2/1965 | Silverman | |
| 3,332,424 A | 7/1967 | Minteer | |
| 3,421,509 A * | 1/1969 | Fiore | A61M 25/0111 606/108 |
| 3,583,391 A | 6/1971 | Cox et al. | |
| 3,866,601 A | 2/1975 | Russell | |
| 3,908,635 A | 9/1975 | Viek | |
| 3,908,663 A | 9/1975 | Viek | |
| 4,109,659 A | 8/1978 | Sheridan | |
| 4,437,857 A | 3/1984 | Goldstein et al. | |
| 4,530,698 A | 7/1985 | Goldstein et al. | |
| 4,652,259 A | 3/1987 | O'Neil | |
| 4,692,154 A * | 9/1987 | Singery | A61M 25/0111 604/271 |
| 4,811,847 A | 3/1989 | Reif et al. | |
| 4,871,358 A | 10/1989 | Gold | |
| 5,163,927 A | 11/1992 | Woker et al. | |
| 5,171,305 A | 12/1992 | Schickling et al. | |
| 5,236,423 A | 8/1993 | Mix et al. | |
| 5,275,177 A | 1/1994 | Wilk | |
| 5,417,666 A | 5/1995 | Coulter | |
| 5,454,798 A | 10/1995 | Kubalak et al. | |
| 5,472,428 A | 12/1995 | Peters | |
| 5,586,968 A | 12/1996 | Grundl et al. | |
| 5,779,670 A | 7/1998 | Bidwell et al. | |
| 5,792,114 A * | 8/1998 | Fiore | A61M 25/0111 604/271 |
| 5,902,286 A | 5/1999 | Reitz | |
| 6,007,521 A | 12/1999 | Bidwell et al. | |
| 6,217,569 B1 | 4/2001 | Fiore | |
| 6,585,721 B2 | 7/2003 | Fiore | |
| 7,255,687 B2 | 8/2007 | Huang et al. | |
| 7,670,331 B2 | 3/2010 | Tanghoej | |
| 10,646,688 B2 * | 5/2020 | Hannon | A61M 25/0017 |
| 2001/0044595 A1 * | 11/2001 | Reydel | A61M 25/0668 604/523 |
| 2005/0015076 A1 | 1/2005 | Giebmeyer et al. | |
| 2005/0049575 A1 | 3/2005 | Snell et al. | |
| 2005/0049576 A1 | 3/2005 | Snell et al. | |
| 2005/0197627 A1 | 9/2005 | Huang et al. | |
| 2006/0163097 A1 | 7/2006 | Murray et al. | |
| 2006/0173422 A1 | 8/2006 | Reydel et al. | |
| 2007/0106233 A1 | 5/2007 | Huang et al. | |
| 2007/0203517 A1 | 8/2007 | Williams et al. | |
| 2008/0097463 A1 * | 4/2008 | House | A61M 25/002 606/108 |
| 2008/0179208 A1 | 7/2008 | Murray et al. | |
| 2008/0228175 A1 | 9/2008 | Snell et al. | |
| 2010/0030197 A1 | 2/2010 | House | |
| 2010/0069852 A1 | 3/2010 | Kelley | |

FOREIGN PATENT DOCUMENTS

| | | |
|---|---|---|
| GB | 2031733 A | 4/1980 |
| WO | WO 92/21399 | 12/1992 |
| WO | WO 2009/012336 A1 | 1/2009 |
| WO | WO 2010/006620 A1 | 1/2010 |

OTHER PUBLICATIONS

Canadian Office Action dated Nov. 17, 2015, for Application No. 2,865,429 entitled: Catheter Assembly Having Protective Sleeve Tip.

Translation of Japanese Office Action dated Jul. 12, 2016, for Japanese Patent Application No. 2014-558944 entitled: Urinary Catheter Assembly.

\* cited by examiner

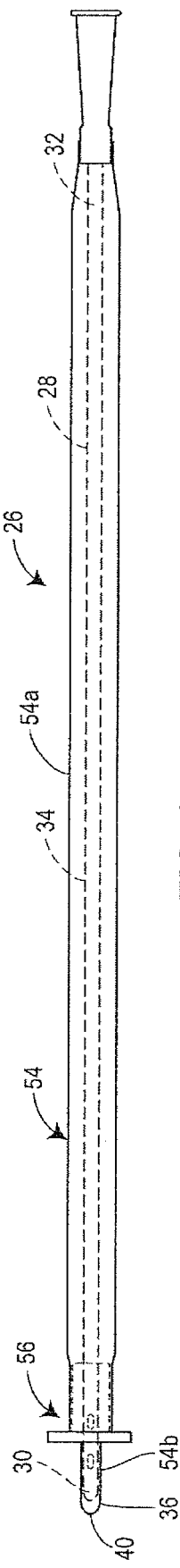
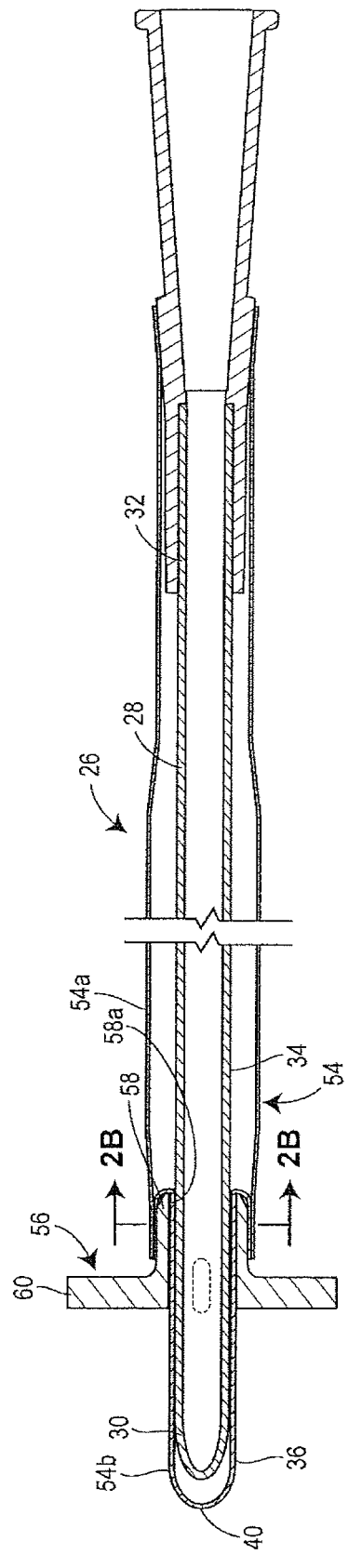
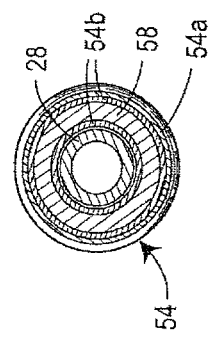
FIG. 2
FIG. 2A
FIG. 2B

FIG. 3
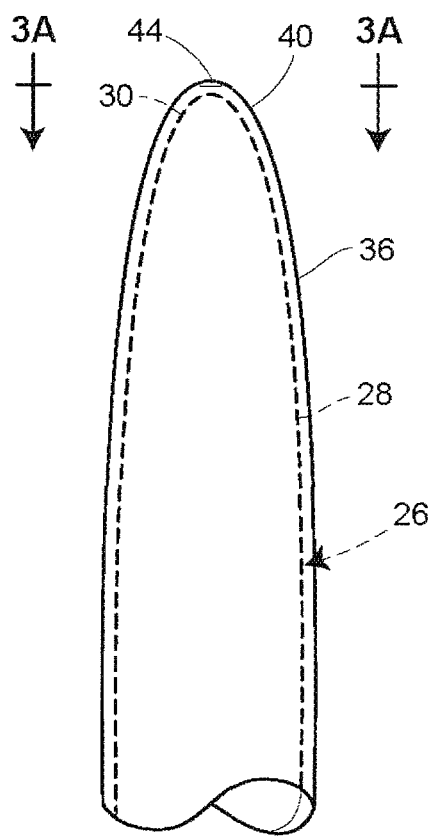
FIG. 4
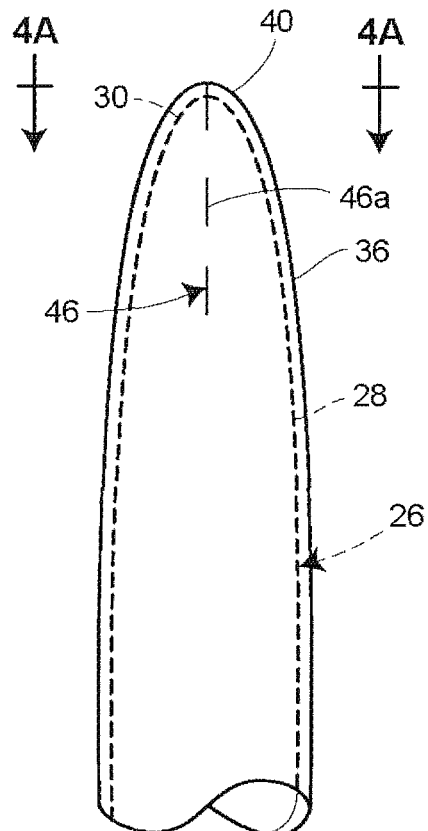
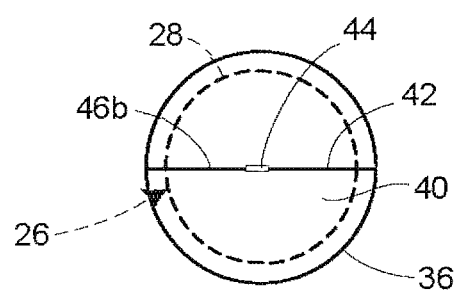
FIG. 3A
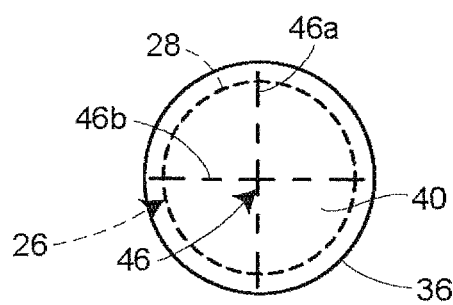
FIG. 4A

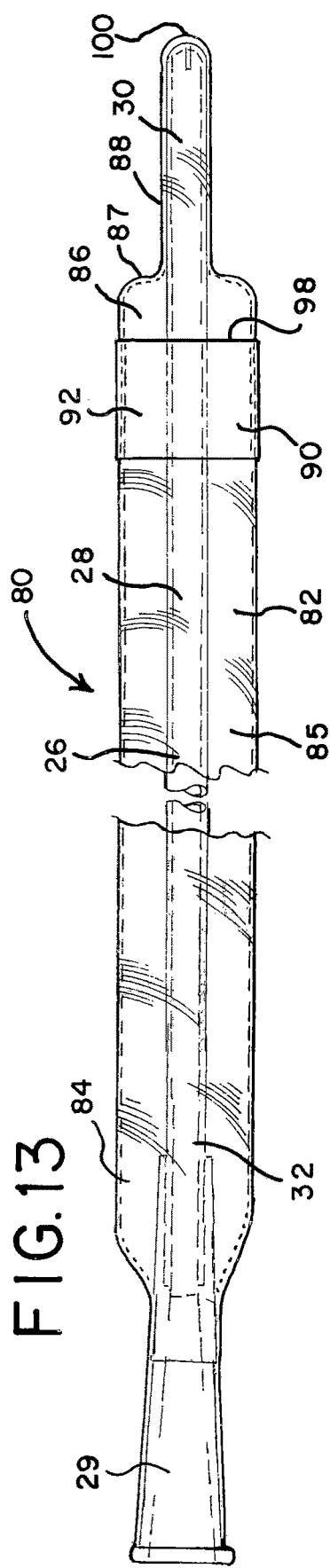
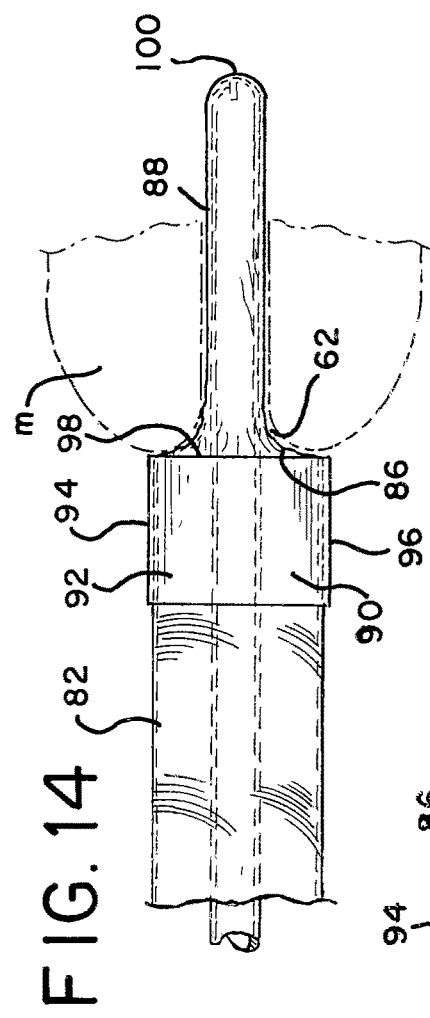
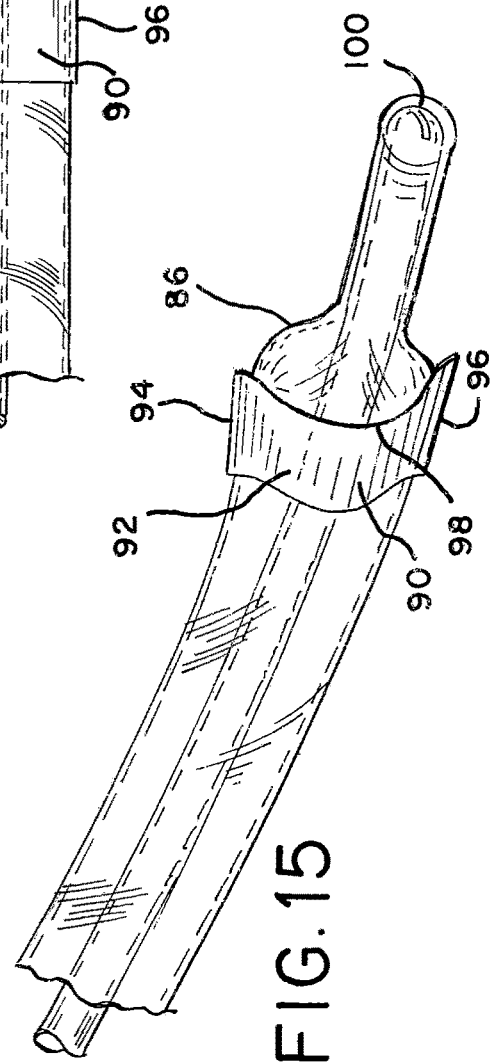

CATHETER ASSEMBLY HAVING PROTECTIVE SLEEVE TIP

RELATED APPLICATIONS

This application is a continuation of U.S. patent application Ser. No. 14/379,161, filed Aug. 15, 2014, which is a U.S. national stage application of PCT Patent Application Serial No. PCT/US2013/027781, filed Feb. 26, 2013, which claims the benefit of and priority to U.S. Provisional Patent Application Ser. No. 61/603,577, filed Feb. 27, 2012 and U.S. Provisional Patent Application Ser. No. 61/701,816, filed Sep. 17, 2012, the contents of which are incorporated by reference herein.

FIELD OF THE DISCLOSURE

The present disclosure is generally directed to a catheter assembly having a catheter shaft for insertion through the urethra for draining urine from the bladder and, more particularly, to a catheter assembly having a protective tip initially confining a proximal insertion end of the catheter shaft until after the protective tip has been inserted into the distal urethra.

BACKGROUND OF THE DISCLOSURE

Catheter assemblies are a good option for many users who suffer from various abnormalities of the urinary system. A common situation is where single use, individually packaged, sterile ready-to-use catheters are utilized. An important criterion for single use, ready-to-use products is that they be entirely user-friendly upon removal from the packaging.

It is quite common for single use, ready-to-use catheters to be provided with a surface treatment which uses a lubricant adapted to reduce friction in order to allow for easier and less traumatic catheter insertion. Currently, there are two major categories of catheters having lubricated surfaces, i.e., so-called "gel-lubricated catheters," having a lubricant applied to the catheter shaft, and catheters having a hydrated hydrophilic outer surface on the catheter shaft.

In a hydrophilic lubricated catheter, the catheter is typically provided with a thin hydrophilic coating adhered to the outer surface of the catheter shaft. Hydrophilic lubricated catheters are activated when a hydrating agent such as water comes into direct contact with the hydrophilic coating on the catheter shaft. When this hydrophilic coating is activated, it provides a low coefficient-of-friction surface to facilitate catheter insertion.

When a catheter is removed from the package for insertion into the urethra, there are some disadvantages encountered. First, when the proximal insertion end of the catheter is introduced into the urethra it may pick up pathogens that are likely to be prevalent in the distal portion of the urethra. These pathogens are then often carried by the proximal insertion end of the catheter into the bladder as it is fully inserted, thereby possibly increasing the risk of infection. Second, the handling of the catheter by the user may also introduce microorganisms onto the surface of the catheter which can cause infection after catheter insertion. For hydrophilic lubricated catheters, these issues must be solved without interfering with activation of the hydrophilic outer surface.

Specifically, for a hydrophilic lubricated catheter, any attempt to: i) prevent pathogens from being picked up by the proximal insertion end of the catheter upon introduction into the distal portion of the urethra, and ii) prevent the introduction of microorganisms onto the surface of the catheter as a result of handling by the user, must be addressed in a manner that does not interfere with the hydrating agent coming into direct contact with the hydrophilic outer surface.

For hydrophilic lubricated catheters, sleeves covering the catheter shaft have not been widely available for a variety of reasons. When they have been provided to protect against contamination from handling of the catheter by the user, they still have failed to remedy the problem of the proximal insertion end picking up pathogens when passing through the distal portion of the urethra during catheter insertion. To address the latter problem, the catheter may be provided with an introducer tip to allow the catheter to bypass the distal portion of the urethra.

While this tends to protect against the delivery of pathogens from the distal portion of the urethra into the bladder, some users have an apprehension about inserting an introducer tip into the urethra during catheterization due to its size. In addition, introducer tips typically have required providing a lubricating gel in the region of the introducer tip as the introducer tip does not typically have a hydrophilic surface, and to ensure there is adequate lubrication of the proximal insertion end of the catheter shaft because, due to its size and material, the introducer tip may inhibit the ability of the hydrating agent to reach the hydrophilic outer surface on the catheter shaft. Thus, there remains a need for a new mechanism to adequately protect the user against delivery of pathogens into the distal portion of the urethra into the bladder without apprehension and with little or no recognition of its existence by the user.

SUMMARY OF THE DISCLOSURE

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a urinary catheter assembly includes a catheter having a catheter shaft with a proximal insertion end and a distal end remote from the proximal insertion end. The assembly also includes a protective sleeve tip covering the proximal insertion end of the catheter shaft. The protective sleeve tip is configured to cover the proximal insertion end of the catheter shaft as the proximal insertion end of the catheter shaft is inserted into a distal portion of the urethra. The proximal insertion end of the catheter shaft is proximally advanceable to rupture the protective sleeve tip and to be advanced through the remainder of the urethra.

In another aspect, a urinary catheter assembly has a catheter including a catheter shaft with a proximal insertion end and a distal end remote from the proximal insertion end. The assembly also includes a protective sleeve covering the catheter shaft wherein the sleeve has a catheter shaft handling portion extending from a point at or near the distal end of the catheter shaft to a point near the proximal insertion end of the catheter shaft. The catheter shaft handling portion accommodates manipulation of the catheter shaft for insertion of the catheter shaft through a urethra. The sleeve also has a rupturable protective sleeve tip covering the proximal insertion end of the catheter shaft. The rupturable protective sleeve tip is configured to cover the proximal insertion end of the catheter shaft as the proximal insertion end of the catheter shaft is inserted into a distal portion of the urethra. The proximal insertion end of the catheter shaft is proximally advanceable to rupture the protective sleeve tip and to be advanced through the remainder of the urethra.

In yet another aspect, a urinary catheter assembly includes a package having a cavity with a catheter therein. The catheter includes a catheter shaft having a proximal insertion end, a distal end remote from the proximal insertion end, and a hydrated hydrophilic outer surface. The assembly also includes a protective sleeve tip covering the hydrated hydrophilic outer surface at the proximal insertion end of the catheter shaft and the protective sleeve tip includes a proximal end with a configuration to initially confine the proximal insertion end of the catheter shaft. The protective sleeve tip is formed of a thin, flexible material capable of conforming to the hydrated hydrophilic outer surface of the proximal insertion end of the catheter shaft. The hydrated hydrophilic outer surface of the catheter shaft facilitates limited movement of the proximal insertion end of the catheter shaft within and relative to the protective sleeve tip while initially being confined by the configuration of the proximal end of the protective sleeve tip. The configuration of the proximal end of the protective sleeve tip resists movement of the proximal insertion end of the catheter shaft beyond the proximal end of the protective sleeve tip.

In another aspect, a hydrophilic urinary catheter assembly includes a gas impermeable package having a sealed cavity with a catheter therein. The catheter includes a catheter shaft having a proximal insertion end, a distal end remote from the proximal insertion end, and a hydrophilic outer surface hydrated by exposure to a vapor hydrating agent in the package. The assembly also includes a vapor permeable sleeve through which the hydrophilic outer surface of the catheter shaft has been exposed to the vapor hydrating agent. The sleeve has a catheter shaft handling portion extending from a point at or near the distal end to a point near the proximal insertion end of the catheter shaft and the catheter shaft handling portion accommodates no-touch gripping of the catheter shaft during insertion of the catheter shaft through the urethra. The sleeve also has a catheter shaft protective sleeve tip portion positioned to at least cover the proximal insertion end of the catheter shaft. The catheter shaft protective sleeve tip portion is adapted to be inserted within the distal portion of the urethra before the catheter shaft is inserted through the urethra. The catheter shaft protective sleeve tip portion closely conforms to the proximal end of the catheter shaft to be supported by and configured to initially confine the proximal insertion end of the catheter shaft until the catheter shaft protective sleeve tip portion has been inserted into the distal portion of the urethra. The vapor permeable sleeve comprises a thin, flexible material covering the hydrophilic outer surface of the catheter shaft to thereby facilitate no-touch gripping and advancement of the catheter shaft, first, through the catheter shaft protective sleeve tip portion after insertion of the catheter shaft protective sleeve tip portion into the distal portion of the urethra and, then, through the remainder of the urethra until the proximal insertion end of the catheter shaft is located within the bladder.

In a further aspect, a hydrophilic urinary catheter assembly includes a gas impermeable package having a sealed cavity with a catheter therein. The catheter includes a catheter shaft having a proximal insertion end, a distal end remote from the proximal insertion end, and a hydrophilic outer surface hydrated by exposure to a vapor hydrating agent in the package. The assembly also includes a vapor permeable sleeve through which the hydrophilic outer surface of the catheter shaft including the proximal insertion end thereof has been exposed to the vapor hydrating agent. The sleeve has a catheter shaft handling portion extending from a point at or near the distal end to a point near the proximal insertion end of the catheter shaft. The catheter shaft handling portion accommodates no-touch gripping of the catheter shaft during insertion of the catheter shaft through the urethra. The sleeve also has a catheter shaft protective sleeve tip portion to be inserted within the distal portion of the urethra before the catheter shaft is inserted through the urethra. The catheter shaft protective sleeve tip portion closely conforms to the proximal end of the catheter shaft to be supported by the proximal insertion end of the catheter shaft and is configured to receive and initially confine the proximal insertion end of the catheter shaft within the sleeve to facilitate insertion of the catheter shaft protective sleeve tip portion into the distal portion of the urethra while at the same time preventing exposure of the catheter shaft to the distal portion of the urethra. The protective sleeve tip portion is swollen and lubricious from exposure to a hydrating agent in the package to facilitate insertion of the proximal end of the protective sleeve tip portion into the distal portion of the urethra. The vapor permeable sleeve comprises a thin, flexible material covering the hydrophilic outer surface of the catheter shaft to thereby facilitate no-touch gripping and advancement of the catheter shaft, first, to cause the proximal insertion end of the catheter shaft to be released from confinement within the sleeve after insertion of the catheter shaft protective sleeve tip portion into the distal portion of the urethra and, then, to cause the catheter shaft to move through the remainder of the urethra until the proximal insertion end of the catheter shaft is located within the bladder.

In yet another aspect, a urinary catheter assembly includes a package having a cavity with a catheter therein. The catheter includes a catheter shaft having a proximal insertion end, a distal end remote from the proximal insertion end, and an outer surface. The assembly including a protective sleeve tip covering the outer surface at the proximal insertion end of the catheter shaft and having a proximal end with a configuration to initially confine the proximal insertion end of the catheter shaft. A quantity of a lubricating agent is located within the package and the protective sleeve tip is exposed to the lubricating agent. The protective sleeve tip is formed of a thin, flexible material that is lubricious when exposed to the lubricating agent and conforms to the outer surface of the proximal insertion end of the catheter shaft. The proximal insertion end of the catheter shaft is arranged for limited movement within and relative to the protective sleeve tip while initially being confined by the configuration of the proximal end of the protective sleeve tip. The configuration of the proximal end of the protective sleeve tip resists movement of the proximal insertion end of the catheter shaft beyond the proximal end of the protective sleeve tip and the protective sleeve tip is lubricious to accommodate limited movement of the catheter shaft within and relative to the protective sleeve tip while at the same time facilitating insertion of the protective sleeve tip into the distal portion of the urethra.

In yet another aspect, a urinary catheter assembly includes a package having a cavity with a catheter therein. The catheter includes a catheter shaft having a proximal insertion end, a distal end remote from the proximal insertion end, and an outer surface. The assembly also includes a protective sleeve tip covering the outer surface at the proximal insertion end of the catheter shaft and has a proximal end with a configuration to initially confine the proximal insertion end of the catheter shaft. The protective sleeve tip is formed of a thin, flexible, inherently lubricious material and conforms to the outer surface of the proximal insertion end of the catheter shaft. The proximal insertion end of the catheter shaft is arranged for limited movement within and relative to the protective sleeve tip while initially being confined by the configuration of the proximal end of the protective sleeve tip. The configuration of the proximal end of the protective sleeve tip resists movement of the proximal insertion end of the catheter shaft beyond the proximal end of the protective sleeve tip, and the protective sleeve tip is lubricious to accommodate limited movement of the catheter shaft within and relative to the protective sleeve tip while at the same time facilitating insertion of the protective sleeve tip into the distal portion of the urethra.

In yet another aspect, a urinary catheter assembly comprises a catheter having a shaft with a proximal insertion end and a distal end spaced from the proximal insertion end. The catheter shaft has a hydrated hydrophilic outer surface. The assembly further comprises a protective sleeve constructed of at least one layer of flexible material extending from the proximal insertion end to the distal end of the catheter shaft and covering the hydrated hydrophilic outer surface of the shaft. At least one additional layer of flexible material overlies at least a portion of the protective sleeve. The assembly further comprises a stop surface defined by the additional layer of flexible material overlying the protective sleeve, the stop surface being located adjacent to the proximal insertion end of the catheter. The additional layer of flexible material may be integral with the protective sleeve or secured to at least part of the protective sleeve by sealing, bonding, molding, adhesive or the like.

BRIEF DESCRIPTION OF THE DRAWINGS

FIG. 2 is a plan view of a first embodiment of a catheter for the ready-to-use catheter assembly of FIG. 1;

FIG. 2A is a cross-sectional view taken along the longitudinal axis of the catheter embodiment of FIG. 2;

FIG. 2B is a cross-sectional view taken generally along the line 2B-2B of FIG. 2A;

FIG. 3 is a plan view of one embodiment of a protective sleeve tip for a catheter;

FIG. 3A is a view of the proximal end of the protective sleeve tip of FIG. 3 taken generally along the line 3A-3A;

FIG. 4 is a plan view of another embodiment of a protective sleeve tip for a catheter;

FIG. 4A is a view of the proximal end of the protective sleeve tip of FIG. 4 taken generally along the line 4A-4A;

FIG. 13 is a plan view of another embodiment of a catheter positioned in a protective sleeve;

FIG. 14 is a side view of the catheter and sleeve of FIG. 13 shown with the catheter tip and protective sleeve tip inserted into the urethra; and FIG. 15 is a perspective view of the catheter and protective sleeve.

DETAILED DESCRIPTION OF THE DISCLOSURE

Figure 1:
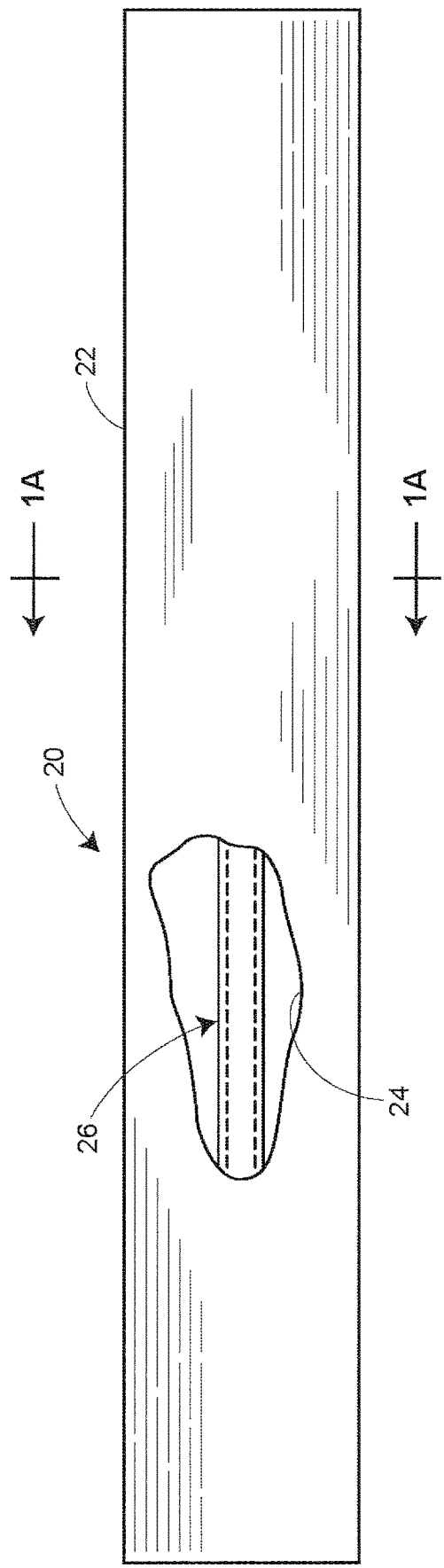
FIG. 1 is a plan view of a ready-to-use catheter assembly in accordance with the present disclosure in which a package is partially broken away to illustrate a catheter therein.

In the illustrations given, and with reference first to FIGS. 1, 1A, 2 and 2A, a ready-to-use urinary catheter assembly 20 comprises a package 22 having a cavity 24 with a catheter 26 contained therein. The catheter 26 includes a catheter shaft 28 having a proximal insertion end 30, a distal end 32 spaced from the proximal insertion end 30 and, optionally, a hydrated hydrophilic outer surface 34. The catheter 26 also includes a rupturable protective sleeve tip 36 formed of a thin, flexible material covering the hydrated hydrophilic outer surface 34 at the proximal insertion end 30 of the catheter shaft 28. The thin, flexible material of the protective sleeve tip 36 is capable of conforming to the hydrated hydrophilic outer surface 34 of the proximal insertion end 30 of the catheter shaft 28. The protective sleeve tip 36 has a rupturable proximal end 40 configured to initially confine the proximal insertion end 30 of the catheter shaft 28 during insertion of the protective sleeve tip into the distal urethra. The proximal insertion end 30 of the catheter shaft 28 is capable of limited movement within and relative to the protective sleeve tip 36 while it is confined by the protective sleeve tip 36. The limited movement is facilitated by the hydrated hydrophilic outer surface 34 which provides a highly lubricious surface within the thin, flexible material of the protective sleeve tip. While initially confined, the proximal end 40 of the protective sleeve tip 36 resists movement of the proximal insertion end 30 of the catheter shaft 28 to a point beyond the proximal end 40 of the protective sleeve tip 36.

With the foregoing, the proximal insertion end 30 of the catheter shaft 28 can be moved within and relative to the protective sleeve tip 36 until it is at or near the proximal end 40 and encounters a resistance to movement. The proximal insertion end 30 of the catheter shaft 28 provides support for the thin, flexible material of the protective sleeve tip 36 which conforms to and covers the proximal insertion end 30 of the catheter shaft 28. As a result, the protective sleeve tip 36 can easily be inserted into the distal urethra and, during insertion, the proximal insertion end of the catheter shaft is covered so it can't be contaminated by pathogens in the distal urethra.

In one exemplary embodiment illustrated in FIGS. 3 and 3A, the configuration of the rupturable proximal end 40 of the protective sleeve tip 36 comprises a slit 42 closed by at least one seal 44 to initially confine the proximal insertion end 30 of the catheter shaft 28 and to thereby also resist movement of the proximal insertion end 30 of the catheter shaft 28 beyond the proximal end 40 of the protective sleeve tip 36 until after the protective sleeve tip 36 has been inserted into the distal portion of the urethra.

In the embodiment of FIGS. 3 and 3A, the catheter shaft 28 can be inserted through the urethra into the bladder following insertion of the protective sleeve tip 36 into the distal portion of the urethra by movement of the proximal insertion end 30 of the catheter shaft 28 against the proximal end 40 of the protective sleeve tip 36 with sufficient force to cause the seal 44 to rupture.

In another exemplary embodiment illustrated in FIGS. 4 and 4A, the configuration of the rupturable proximal end 40 of the protective sleeve tip 36 comprises a perforation 46 initially confining the proximal insertion end 30 of the catheter shaft 28. The perforation 46 permits limited movement of the proximal insertion end 30 of the catheter shaft 28 within and relative to the protective sleeve tip 36. However, the perforation 46 also serves to resist movement of the proximal insertion end 30 of the catheter shaft 28 to a point beyond the proximal end 40 of the protective sleeve tip 36. The perforation 46 further permits the proximal insertion end 30 of the catheter shaft 28 to move to a point beyond the proximal end 40 of the protective sleeve tip 36 by rupturing the perforation 46 with sufficient force. As shown, the perforation 46 is formed of two cross-perforations 46a and 46b to divide the protective sleeve tip 36 into four equal quadrants although other perforation patterns can be used as will be apparent to those skilled in the art.

In the embodiment of FIGS. 4 and 4A, the catheter shaft 28 can be inserted through the urethra into the bladder following insertion of the protective sleeve tip 36 into the distal portion of the urethra by movement of the proximal insertion end 30 of the catheter shaft 28 against the proximal end 40 of the protective sleeve tip 36 with sufficient force to cause the perforation 46 to rupture.

Figure 5:
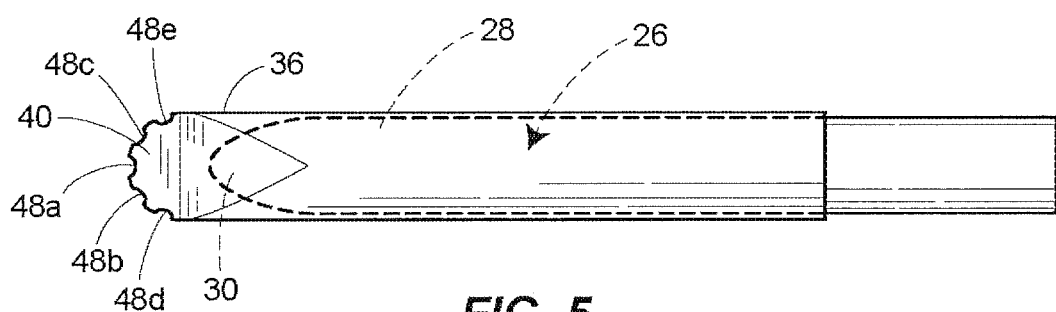
FIG. 5 is a plan view of another embodiment of a protective sleeve tip for a catheter.
Figure 5A:
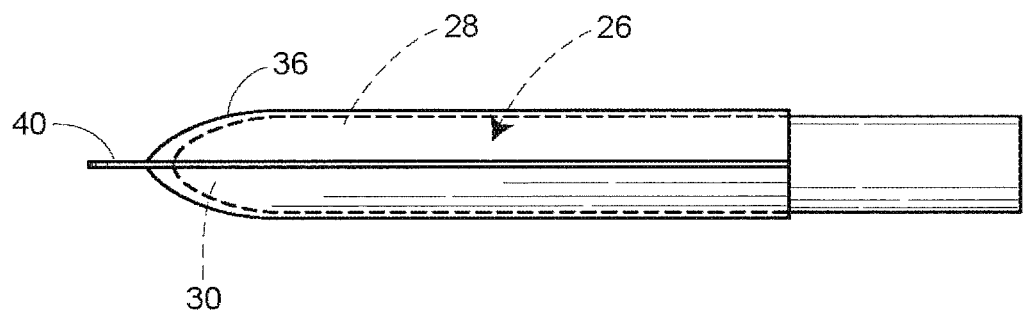
FIG. 5A a side elevational view of the protective sleeve tip of the embodiment of FIG. 5.

In three other embodiments illustrated in FIGS. 5 and 5A, the configuration of the rupturable proximal end 40 of the protective sleeve tip 36 comprises a generally semi-cylindrical shape terminating in either a single opening 48a smaller than the diameter of the catheter shaft 28, or three openings 48a, 48b, 48c, or five openings 48a, 48b, 48c, 48d, 48e, each smaller than the diameter of the catheter shaft 28. The generally semi-cylindrical shape and the opening(s) cause the proximal insertion end 30 of the catheter shaft 28 to be initially confined for limited movement within and relative to the protective sleeve tip 36. The generally semi-cylindrical shape and the opening(s) also resist movement of the proximal insertion end 30 of the catheter shaft 28 to a point beyond the proximal end 40 of the protective sleeve tip 36 but permit the proximal insertion end 30 of the catheter shaft 28 to move to a point beyond the proximal end 40 of the protective sleeve tip 36 by penetrating through the opening(s) with sufficient force.

In the three embodiments generally illustrated in FIGS. 5 and 5A, the catheter shaft 28 can be inserted through the urethra into the bladder following insertion of the protective sleeve tip 36 into the distal portion of the urethra by movement of the proximal insertion end 30 of the catheter shaft 28 against the proximal end 40 of the protective sleeve tip 36 with sufficient force to penetrate through the single opening 48a, or the three openings 48a-48c, or the five openings 48a-48e by rupturing the proximal end 40 of the protective sleeve tip 36 to move beyond it.

Figure 6:
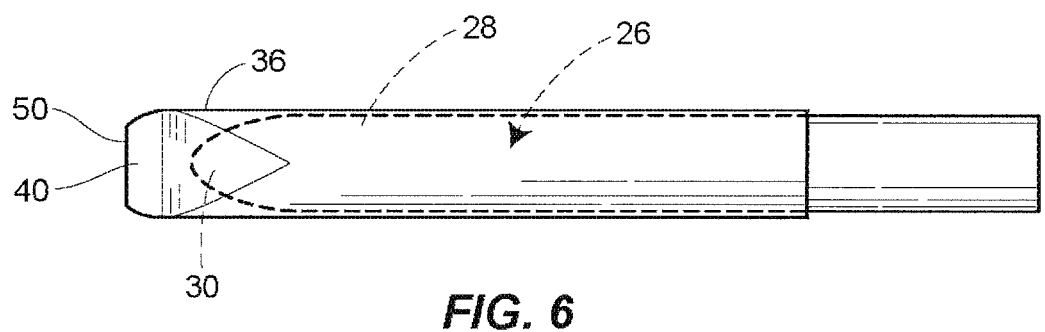
FIG. 6 is a plan view of another embodiment of a protective sleeve tip for a catheter.
Figure 6A:
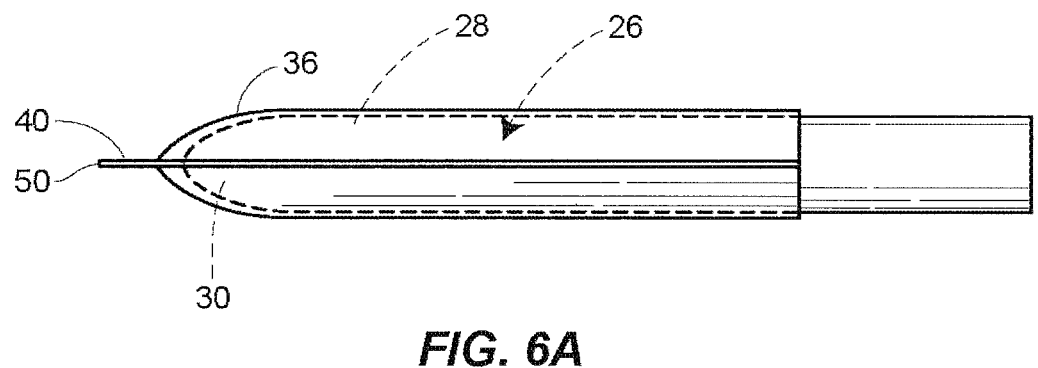
FIG. 6A is a side elevational view of the protective sleeve tip of the embodiment of FIG. 6.

In still another exemplary embodiment illustrated in FIGS. 6 and 6A, the configuration of the rupturable proximal end 40 of the protective sleeve tip 36 comprises an inwardly curved shape terminating in a linear opening 50 shorter in length than the diameter of the catheter shaft 28. The inwardly curved shape and the linear opening 50 cause the proximal insertion end 30 of the catheter shaft 28 to be initially confined for limited movement within and relative to the protective sleeve tip 36 and, in addition, to resist movement of the proximal insertion end 30 of the catheter shaft 28 to a point beyond the proximal end 40 of the protective sleeve tip 36. However, the inwardly curved shape and the linear opening 50 further permits the proximal insertion end 30 of the catheter shaft 28 to move to a point beyond the proximal end 40 of the protective sleeve tip 36 by penetrating through the linear opening 50 with sufficient force.

In the embodiment illustrated in FIGS. 6 and 6A, the catheter shaft 28 can be inserted through the urethra into the bladder following insertion of the protective sleeve tip 36 into the distal portion of the urethra by movement of the proximal insertion end 30 of the catheter shaft 28 against the proximal end 40 of the protective sleeve tip 36 with sufficient force to rupture the proximal end 40 by penetrating through the linear opening 50.

Figure 7:
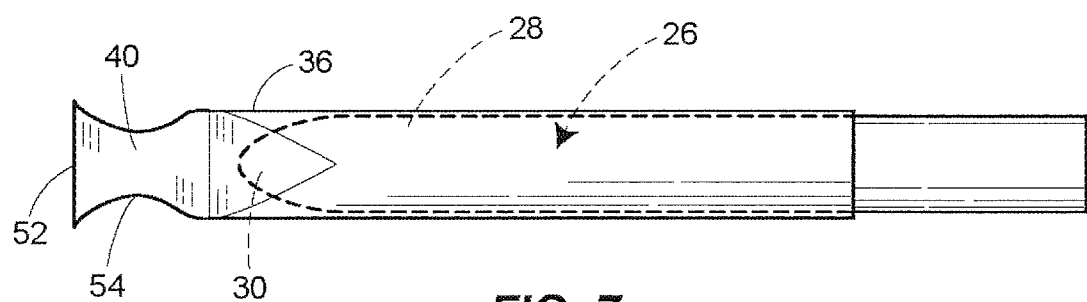
FIG. 7 is a plan view of another embodiment of a protective sleeve tip for a catheter.
Figure 7A:
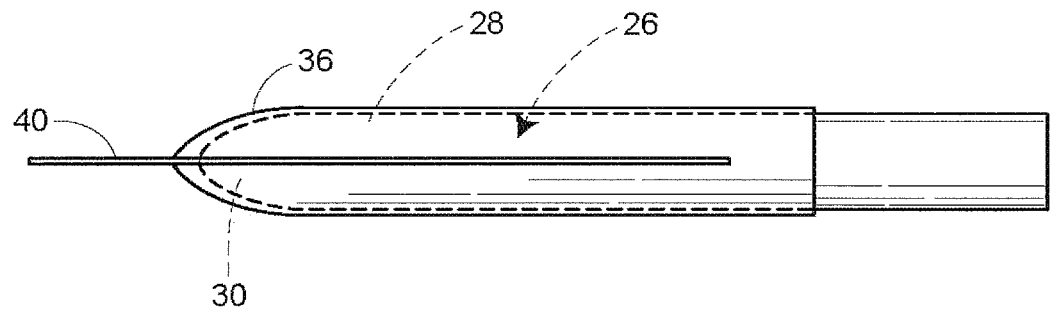
FIG. 7A is a side elevational view of the protective sleeve tip of the embodiment of FIG. 7.

In yet another exemplary embodiment illustrated in FIGS. 7 and 7A, the configuration of the rupturable proximal end 40 of the protective sleeve tip 36 comprises an hour glass shape terminating in a linear opening 52 and having a minimum hour glass spacing at 54 less than the diameter of the catheter shaft 28. The hour glass shape and the linear opening 52 cause the proximal insertion end 30 of the catheter shaft 28 to be initially confined for limited movement within and relative to the protective sleeve tip 36 and, also, to resist movement of the proximal insertion end 30 of the catheter shaft 28 beyond the proximal end 40 of the protective sleeve tip 36. The hour glass shape and the linear opening 52 further permit the proximal insertion end 30 of the catheter shaft 28 to move to a point beyond the proximal end 40 of the protective sleeve tip 36 by penetrating through the minimum hour glass spacing at 54 and the linear opening 52 with sufficient force.

In the embodiment illustrated in FIGS. 7 and 7A, the catheter shaft 28 can be inserted through the urethra into the bladder following insertion of the protective sleeve tip 36 into the distal portion of the urethra by movement of the proximal insertion end 30 of the catheter shaft 28 against the proximal end 40 of the protective sleeve tip 36 with sufficient force to rupture the proximal end 40 by penetrating through the minimum hour glass spacing and the linear opening 52.

In other respects, the protective sleeve tip may advantageously have an outer surface with a hydrated hydrophilic coating thereon facilitating insertion of the proximal end 40 of the protective sleeve tip 36 into the distal portion of the urethra.

In the various embodiments, a quantity of a hydrating agent or, alternatively, a lubricating agent is located within the package 22 and the protective sleeve tip 36 is preferably swollen and/or lubricious from exposure to the hydrating or lubricating agent. This feature serves to facilitate the ease and comfort of inserting the proximal end 40 of the protective sleeve tip 36 into the distal portion of the urethra. The protective sleeve tip 36 material may be selected from a group consisting of polyurethane and polyethylene, e.g., a polyurethane film and a polyethylene film and, preferably a polyurethane film or other materials set forth below.

With regard to the hydrating agent within the package 22, it advantageously forms a 100% relative humidity atmosphere within the package in order to expose the protective sleeve tip 36 to this atmosphere so it is swollen and lubricious at the time the package is opened.

Preferably, since the protective sleeve tip 36 will come into contact with the sensitive tissues of the distal portion of the urethra, the polyurethane film is a polyether aliphatic based film suitable for skin contact. Also, the polyurethane film may advantageously have a moisture vapor transmission rate between 900 and 11,000 g/m2/24 hrs. Still more preferably, the moisture vapor transmission rate of the polyurethane film may be approximately 3000 g/m2/24 hrs.

As for other details, the polyurethane film preferably may have a thickness between 0.5 and 35.0 mils and, preferably, approximately 1 mil. While discussed relative to the protective sleeve tip 36, these materials and parameters may also apply to the sleeve 54 discussed below.

Referring again to FIGS. 2 and 2A, the catheter 26 may include a vapor permeable sleeve 54 through which the hydrophilic outer surface 34 of the catheter shaft 28 has been exposed to a vapor hydrating agent 55 in the package 22 (FIG. 1). The sleeve 54 may also include a catheter shaft handling portion 54a extending from a point at or near the distal end 32 to a point remote therefrom and generally near to the proximal insertion end 30 of the catheter shaft 28 for no-touch gripping of the catheter shaft 28. The sleeve 54 may have a catheter shaft protective sleeve tip portion 54b comprising the protective sleeve tip 36 to be inserted within the distal portion of the urethra and positioned to at least cover the proximal insertion end 30 of the catheter shaft 28.

In this embodiment, the vapor permeable sleeve 54 comprises a thin, flexible material covering the hydrophilic outer surface 34 of the catheter shaft 28 to thereby facilitate no-touch gripping and advancement of the catheter shaft 28, first, through the catheter shaft protective sleeve tip portion 54b after insertion of the catheter shaft protective sleeve tip portion 54b into the distal portion of the urethra and, then, through the remainder of the urethra until the proximal insertion end 30 of the catheter shaft 28 is located within the bladder.

As will be appreciated, the catheter shaft protective sleeve tip portion 54b comprises the protective sleeve tip 36 previously described, and it can either be a component associated with but distinct from the catheter shaft handling portion 54a or it can be part of a single continuous sleeve comprised of a catheter shaft handling portion 54a and a catheter shaft protective sleeve tip portion 54b.

Figure 1A:
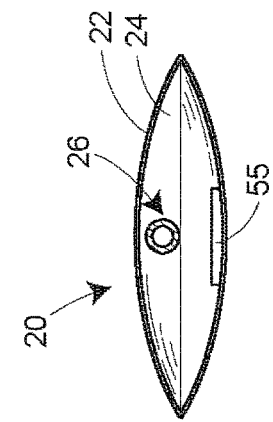
FIG. 1A is a cross-sectional view taken generally along the line 1A-1A in FIG. 1 illustrating the interior cavity of the package including a vapor hydrating agent therein.

Referring to FIG. 1A, the vapor hydrating agent 55 in the package 22 may comprise a strip of material exhibiting wicking or high capillary action and holding and retaining liquid water. Preferably, the package 22 is formed of a gas and liquid impermeable material to prevent the liquid water in the strip of material from drying out and to promote a change of phase over time to in order to provide and maintain a vapor atmosphere within the package 22. Additionally, it may be desirable to provide a mid-package gas permeable, liquid impermeable membrane to separate the catheter 26 from the strip of material which holds and retains the liquid water.

Over time, at least some of the liquid water held and retained in the strip of material will change phase into a vapor, pass through the mid-package gas permeable, liquid impermeable membrane and will pass through the vapor permeable sleeve 54 including the catheter shaft handling portion and the catheter shaft protective sleeve portion to hydrate the hydrophilic outer surface 34 from the distal end 32 entirely to the proximal insertion end 30 so the catheter 26 is in a ready-to-use condition when the user receives the package 22.

Figure 11:
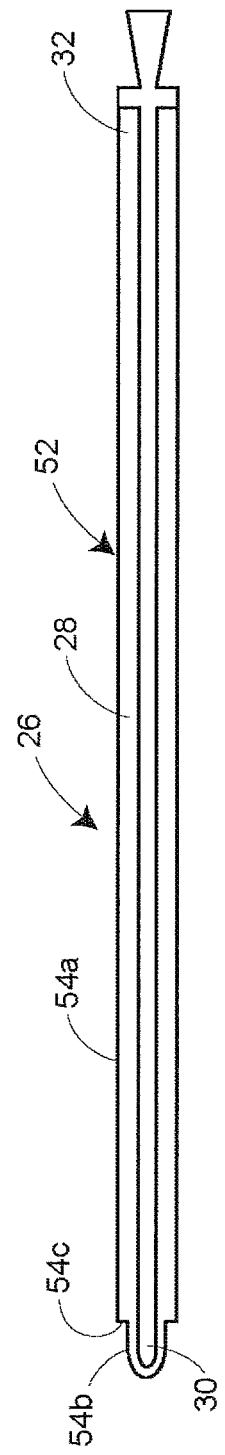
FIG. 11 is a plan view of a second embodiment of a catheter for the ready-to-use catheter assembly of FIG. 1.

With regard to the embodiment which is illustrated in FIG. 11, the catheter shaft handling portion 54a and the catheter shaft protective sleeve tip portion 54b will be seen to comprise a single continuous sleeve 54 extending from a distal end point at or near the distal end 32 of the catheter shaft 28 to a proximal end point beyond the proximal insertion end 30 of the catheter shaft 28. However, in the preferred embodiment illustrated in FIGS. 2 and 2A, the catheter shaft handling portion 54a and the catheter shaft protective sleeve tip portion 54b each advantageously comprise separate sleeve segments each joined to an introducer flange 56. In the latter embodiment, it will be seen that the separate sleeve segments 54a and 54b, i.e., the catheter shaft handling portion 54a and the catheter shaft protective sleeve tip portion 54b of the vapor permeable sleeve 54, are each joined to the introducer flange 56 which may advantageously be located generally at or near the proximal insertion end 30 of the catheter shaft 28.

Referring once again to the embodiment illustrated in FIG. 11, it will be seen to omit the introducer flange 56 and, instead, the catheter shaft handling portion 54a is oversized relative to the catheter shaft protective sleeve tip portion 54b which closely conforms to the size and shape of the proximal insertion end 36 of the catheter shaft 28, and the two portions 54a and 54b are integral with one another in a transition area 54c of the sleeve 54.

Advantageously, the introducer flange 56 includes a tubular portion 58 having an opening 58a to receive the catheter shaft 28 and a flange portion 60 surrounding the tubular portion 58 to serve as a stop upon insertion of the catheter shaft protective sleeve tip portion 54b into the distal portion of the urethra. The tubular portion 58 preferably extends in the direction of the distal end 32 of the catheter shaft 28 and the catheter shaft protective sleeve tip portion 54b is preferably secured to the outer surface of the tubular portion 58 (FIG. 2B) and reversely extends through the tubular portion 58 in the direction of and beyond the flange portion 60. The catheter shaft handling portion 54a may then advantageously be secured to the previously secured catheter shaft protective sleeve tip portion 54b (FIG. 2B) on the outer surface of the tubular portion 58 and extend in a direction opposite the flange portion 60 to a point near the distal end 32 of the catheter shaft 28.

Figure 10:
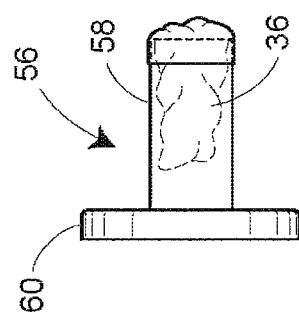
FIG. 10 is a side elevational view illustrating the protective sleeve tip contained within an introducer flange.

The catheter shaft protective sleeve tip portion 54b is advantageously formed to be of a length which is sufficient to extend entirely through the tubular portion 58 of the introducer flange 56 and to a point located beyond the flange portion 60 by a distance sufficient to entirely traverse the distal urethra as shown in FIG. 2A. Alternatively, the catheter shaft protective sleeve tip portion 54b may be formed of this length but initially reverse folded or rolled so as to be fully contained within the tubular portion 58 of the introducer flange 56 (FIG. 10), and later unfolded or unrolled to extend the catheter shaft protective sleeve tip portion 54b by advancing the catheter shaft 28 to the position shown in FIG. 2A for traversing the distal urethra.

In the latter case, the proximal insertion end 30 of the catheter shaft 28 will cause the reverse folded catheter shaft protective sleeve tip portion 54b to unfold or unroll and extend in a position for insertion into the distal urethra where it closely conforms to and covers the proximal insertion end 30 of the catheter shaft 28 as shown in FIG. 2A.

As previously described, a quantity of a hydrating or lubricating agent is located within the package 22 and the catheter shaft protective sleeve tip portion 54b is preferably swollen and/or lubricious from exposure thereto. In addition to facilitating the ease and comfort of inserting the catheter shaft protective sleeve tip portion 54b into the distal portion of the urethra, the unfolding or unrolling of the protective sleeve tip portion 54b is also facilitated.

Figure 12:
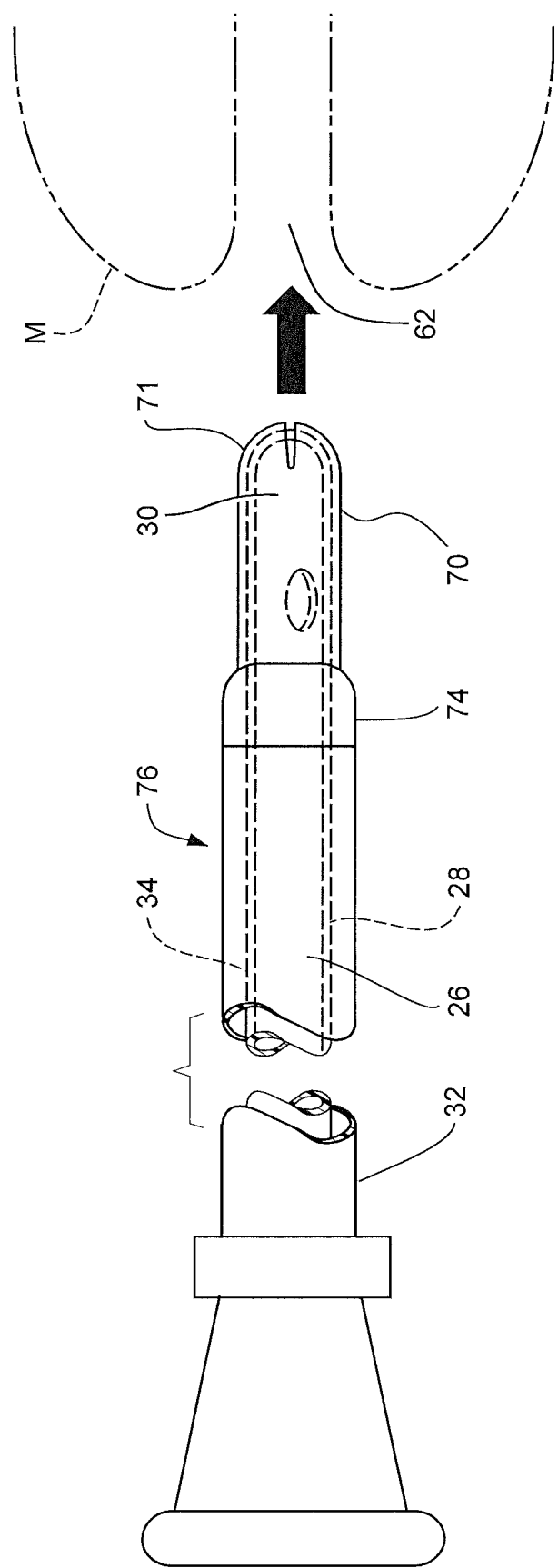
FIG. 12 is a side view of another embodiment of a catheter positioned in a protective sleeve and protective sleeve tip for insertion into the distal urethra.

Yet another exemplary embodiment of a catheter is illustrated in FIG. 12. As with FIG. 11, introducer flange 56 is omitted in the embodiment of FIG. 12. Instead, a layer of material is provided in place of flange 56. This layer of material serves the function of a flange in that it preferably serves as a "stop" upon insertion of the catheter shaft protective sleeve tip portion 70 and limits the distance of insertion of a catheter proximal insertion end into the distal portion of the urethra.

In particular, as shown in FIG. 12, catheter 26 includes a catheter shaft 28 having a proximal insertion end 30 and a distal end 32 spaced from the proximal insertion end 30. The catheter shaft also preferably includes a hydrophilic outer surface 34 as described above in connection with prior embodiments. A protective sleeve tip 70 covers the hydrophilic outer surface 34 of the proximal insertion end 30 of the catheter shaft 28. The proximal insertion end 30 of the catheter shaft 28 provides support for the protective sleeve tip 70 which conforms to and covers the proximal insertion end 30 of the shaft 28, such that the protective sleeve tip 70 can be inserted into the distal urethra. Preferably, the protective sleeve tip 70 is configured to initially confine the proximal insertion end 30 of catheter shaft 28 during insertion of the protective sleeve tip 70 into the distal urethra and also covers the insertion end of the catheter so it is not contaminated by pathogens in the distal urethra.

It will also be appreciated that the protective sleeve tip 70 includes a proximal end 71 that covers and initially confines the proximal insertion end 30 of the catheter shaft 28 and also resists movement of the proximal insertion end of the catheter beyond the proximal end 71 of the protective sleeve tip until after the tip has been inserted into the distal portion of the urethra. The catheter shaft 28 can be inserted through the urethra into the bladder following insertion of the protective sleeve tip 70 into the distal portion of the urethra by movement of the proximal insertion end 30 of the catheter shaft 28 against the proximal end 71 of the protective sleeve tip 70 with sufficient force to cause the proximal end 71 of the tip to rupture. The structure of the proximal end 71 and the configuration of the rupturable portion may vary, and can include, for example, one or more of the exemplary embodiments described above and illustrated in FIGS. 3-7A. Preferably, proximal end 71 comprises a slit, perforation or opening closed by at least one seal to initially confine the catheter proximal insertion end 30, which slit or opening can be ruptured by moving insertion end 30 against the proximal end 71 with sufficient force.

The protective sleeve tip 70 may be constructed from various materials, including monolayer and/or co-extruded films, such as polyurethane and/or polyethylene film, with a thickness and vapor transmission rate similar to that mentioned above in connection with previously described embodiments. However, other materials having differing characteristics and parameters are also contemplated. Preferably, the protective sleeve tip 70 may be constructed of multiple layers of material, such as, for example, two layers of the material or film. In one example, the protective sleeve tip 70 may be formed from two layers of Mylan® film material offered by Mylan Technologies of St. Albans, Vt. The protective sleeve tip 70 may be up to about 50 mm in length and up to about 40 mm in diameter. More preferably, the tip may be about 20-30 mm in length and about 20 mm in diameter. It is advantageous that the protective sleeve tip have an outer surface with a hydrated hydrophilic coating thereon to facilitate insertion of the tip 70 into the distal portion of the urethra.

Referring to FIG. 12, the catheter 26 also preferably includes a sleeve 72. It is desirable for the sleeve 72 to be vapor permeable through which the hydrophilic outer surface 34 of the catheter shaft is exposed to a vapor hydrating agent present in the catheter packaging, such as packaging 22 as illustrated in FIG. 1. The sleeve 72 provides a "no-touch" gripping surface for the user so that the catheter shaft 28 is not exposed to direct handling by the user and/or contaminants in the external environment before and during insertion. The materials described above with respect to the protective sleeve tip 70 may also apply and be used to construct the sleeve 72. In particular, it is preferable that sleeve 72 be constructed of one or multiple layers of material (e.g. Mylan film) such as two layers of the material or film for example. As FIG. 12 illustrates, a wider portion 76 of sleeve 72 may extend from the catheter distal end 32 to a point at or near where the sleeve tapers into a more narrow diameter that defines protective tip 70 or where sleeve 72 otherwise meets the protective tip 70. For example, the wider portion 76 of sleeve 72 may extend from the catheter distal end 32 to a point that is approximately 20 mm from the protective sleeve tip proximal end 71.

In one embodiment, protective sleeve tip 70 may be integral with sleeve 72, such that the tip and sleeve comprise a single continuous structure extending from the proximal insertion end 30 to the distal portion 32 of the catheter 26. However, it is also contemplated that the protective sleeve tip 70 and sleeve 72 are separate structures that can be joined together. In the latter embodiment, the tip 70 and sleeve 72 may be joined together, for example, at or near the point where the wider section 76 of sleeve 72 meets the more narrow or tapered portion that defines protective sleeve tip 70.

As further illustrated in FIG. 12, one or more additional layers of flexible material may be secured to sleeve 72. In one embodiment, the additional layer of material may extend from a point at or near the protective sleeve tip to the catheter distal end, however, more preferably, the additional layer of material comprises a segment of material or flange portion, adjacent the protective sleeve tip 70. More particularly, it is preferable that the flange portion or segment is a band of material 74 positioned at a point where the wider portion 76 of sleeve 72 narrows or tapers into a smaller diameter that defines protective tip 70 or where sleeve 72 otherwise meets or joins protective tip 70. In one example, the band of material comprises at least one layer of film that is integral with, or alternatively, is secured to at least a portion of sleeve 72. The material may be secured to sleeve 72 by various methods, such as sealing, bonding, molding, adhesive or the like. The band of material 74 may be approximately 10 mm wide and sealed to sleeve 72 approximately 20-30 mm from the protective tip proximal end 71, although, it is also contemplated that the band of material 74 is comprised of more than a single layer of material and may be positioned at any point closer to or farther away from the catheter proximal insertion end, as may be desired or required for a particular use.

It will be appreciated that the band of material 74 comprises a radially extending multiple layer film assembly which provides a "stop" surface. In other words, the band of material 74 comprises at least one layer secured to at least a portion of the material that makes up sleeve portion 72, therefore resulting in a multiple layer assembly. More specifically, in a preferred embodiment, sleeve 72 comprises two layers of material or film, while band of material 74 comprises one layer of material or film bonded or sealed to sleeve 72, thus forming an assembly of at least three layers of material at segment or band 74. In one embodiment, the band of material 74 may be constructed from various materials including those already described above in connection with the sleeve and protective sleeve tip. However, it is also contemplated that band of material 74 may be constructed of other materials having different characteristics and/or parameters. More specifically, the material may differ in thickness, rigidity, flexibility and permeability as compared to the materials that make up the sleeve and/or protective sleeve tip. In any event, it is preferable that during use, the protective tip 70 (and the catheter proximal insertion end 30 covered by the protective tip) can be inserted or advanced into the urethral opening only a limited distance until the stop surface provided by the band of material 74 abuts the meatus M of the penis (or the urethral opening for females, not shown). As such, the band of material 74 serves the stop function of an introducer flange, (i.e. such as flange 56, 60 described herein).

The described embodiment illustrated in FIG. 12 provides several advantages. For example, the necessity for an additional molded flange component as well as the need for assembling and/or bonding a separate flange component to the catheter 26 is eliminated, thus simplifying manufacturing and assembly processes without compromising functionality. Use of a band of material 74 sealed or bonded to at least part of one or both of a protective sleeve tip and sleeve essentially incorporates the "stop" function of a flange-like structure into a simplified and streamlined design that, from the perspective of the user who requires catheterization, is easy to use and may be visually less intimidating.

Figure 8:
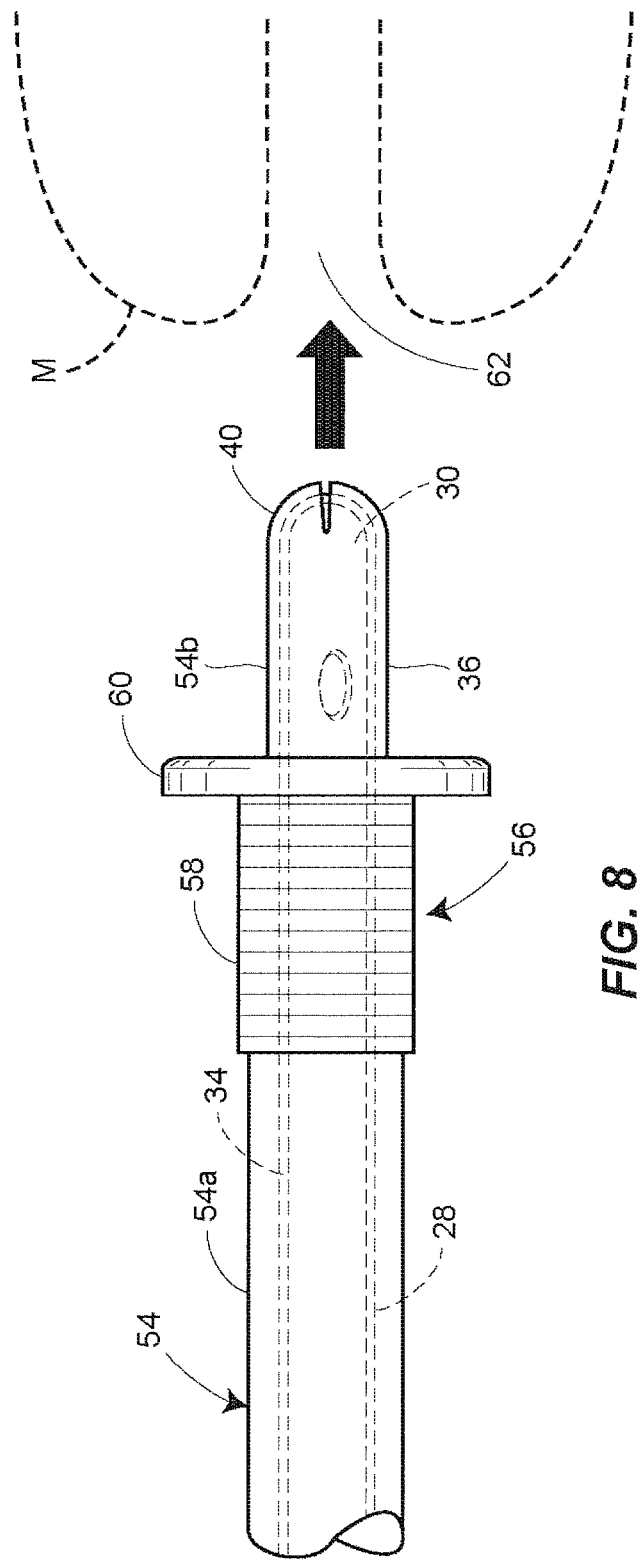
FIG. 8 is a side elevational view illustrating a catheter positioned in a protective sleeve tip for insertion into the distal urethra.
Figure 9:
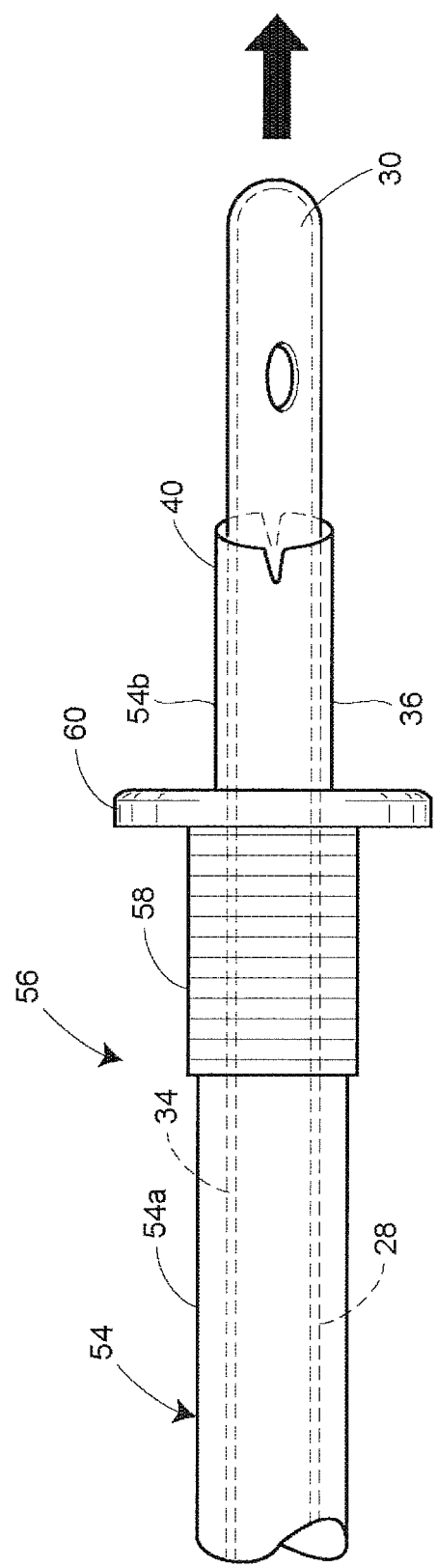
FIG. 9 is a side elevational view of the catheter of FIG. 8 after penetration of the catheter through the protective sleeve tip.

Referring now to FIGS. 8 and 9, the manner in which all of the foregoing embodiments are used can be best understood. If the proximal insertion end 30 of the catheter shaft 28 is not already positioned as shown, the catheter shaft 28 is gripped through the catheter shaft handling portion 54a or sleeve 72 and advanced toward the proximal end 40, 71 of the protective sleeve tip 36, 70 or catheter shaft protective sleeve tip portion 54b until resistance to movement is felt. At this point, the user may grip the tubular portion 58 or the flange portion 60 of the introducer flange 56 or alternatively, grip the catheter sleeve 72 at or near band of material 74.

Once the user has gripped one of the portions of the introducer flange or the sleeve 72 near band 74, the proximal end 40, 71 of the protective sleeve tip 36, 70 or the catheter shaft protective sleeve tip portion 54b can be advanced for insertion into the urethral opening 62 until the stop surface of the flange portion 60 or band of material 74 rests against the meatus M of the penis (or the urethral opening for females, not shown). The protective sleeve tip 36, 70 or catheter shaft protective sleeve tip portion 54b will line the distal urethra while still covering the proximal insertion end of catheter shaft 28 so that it cannot become exposed to pathogens located in the distal urethra. The user can grip the catheter shaft 28 through the catheter shaft handling portion 54a or sleeve 72 and exert a force to cause the proximal insertion end 30 of the catheter shaft 28 to rupture or otherwise pass through the proximal end 40, 71 of the protective sleeve tip 36, 70 or catheter shaft protective sleeve tip portion 54b.

FIGS. 13-15 illustrate another embodiment of a catheter assembly 80 of the present disclosure. In catheter assembly 80, catheter 26 is covered by a protective sleeve 82 which provides a no-touch gripping of catheter 26 as described above. Catheter 26 has the same or similar features as described above and preferably, but not necessary, includes a hydrophilic outer coating.

Protective sleeve 82 includes a distal end portion 84 and a proximal end portion 86 which includes a protective proximal end sleeve tip 88. The protective sleeve 82 also includes a catheter shaft handling portion 85 through which the user may grip and manipulate the catheter shaft 28. The protective sleeve tip 88 may be smaller in cross-section than the rest of protective sleeve 82. Preferably, the cross-section of sleeve tip 88 is slightly bigger than the proximal end insertion end 30 of catheter shaft 28 so as to snugly fit thereover. Also, the sleeve tip 88 may be merged or joined with the rest of sleeve 82 at transition area 87, which may be in the form of a shoulder.

The protective sleeve 82 and sleeve tip 88 may be constructed from various materials, including monolayer and/or co-extruded films, such as polyurethane and/or polyethylene film, with a thickness and vapor transmission rate similar to that mentioned above in connection with previously described embodiments. However, other materials having differing characteristics and parameters are also contemplated. For example, the protective sleeve 82 and sleeve tip 88 may be constructed of multiple layers of material, such as, for example, two layers of the material or film. In one particular example, the protective sleeve tip 88 may be formed from two layers of Mylan® film material offered by Mylan Technologies of St. Albans, Vt. Sleeve tip 88, optionally, may have an outer hydrophilic surface that is highly lubricous when hydrated to facilitate the insertion of the sleeve tip 88 into the urethral opening 62 (FIG. 14). Additionally, when a hydrophilic catheter is employed, it is desirable for the protective sleeve 82 to be vapor permeable through which the hydrophilic outer surface of the catheter shaft 28 is exposed to a vapor hydrating agent present in the catheter packaging, such as packaging 22 as illustrated in FIG. 1. Sleeve tip 88 and the rest of protective sleeve 82 may be of a one-piece construction or may be made from two separate components that are joined together at transition area 87. In one example, protective sleeve 82 may be made of a material that is configured for vapor transmission for hydrating a hydrophilic catheter and/or for no-touch gripping of catheter shaft 28 while sleeve tip 88 may be made of a material that is configured for insertion into the distal opening of the urethra.

Referring to FIG. 13, the distal end portion 84 of protective sleeve 82 may be affixed or connected to a connection member, such as funnel 29, located at the distal end portion 32 of the catheter shaft 28. In an alternative embodiment, the distal end portion 84 of protective sleeve 82 may be affixed or connected to the distal end portion 32 of catheter shaft 28. The distal end portion 84 may be affixed to funnel 29 or the distal end 32 of catheter shaft 28 in any suitable manner, such as by heat sealing, welding or adhesive. Preferably, distal end portion 84 of protective sleeve 82 itself and/or the connection between distal end portion 84 and the funnel 29 or distal end portion 32 of catheter 28 includes vents that allow air to move out of the protective sleeve 82 as the catheter is advanced out of the sleeve 82 and the sleeve collapses.

Referring to FIGS. 13 and 15, the proximal end portion 86 of protective sleeve 82 includes a stop member 90 adjacent to sleeve tip 88. The stop member 90 is defined by a band or strip of material 92 that is attached or affixed 82 along edges 94 and 96 of the band of material to the distal end portion 86 of the protective sleeve. The proximal edge 98 of the band of material 92 is not attached to the protective sleeve 82 and defines or provides a "stop" surface that abuts the meatus M of the penis (or the urethral opening for females, not shown) to prevent further insertion of the protective sleeve 82 into the urethral opening 62, as illustrated in FIG. 14. In the illustrated embodiment, sleeve 82 includes one band or strip of material 92 that extends over one side of the sleeve. In an alternative embodiment, the sleeve may include a second band or strip of material that extends over the other side of the sleeve 82.

The band of material 92 is preferably a thin film that may be constructed from various materials including those already described above in connection with the sleeve and protective sleeve tip. However, it is also contemplated that band of material 92 may be constructed of other materials having different characteristics and/or parameters. More specifically, the material may differ in thickness, rigidity and flexibility as compared to the materials that make up the sleeve and/or protective sleeve tip.

The proximal insertion end 30 of catheter shaft 28 provides support for the protective sleeve tip 88 which conforms to and covers the proximal insertion end 30 of catheter shaft 28, such that the protective sleeve proximal tip 88 is inserted into the urethral opening 62 with the proximal insertion end 30 of catheter shaft 28. The sleeve tip 88 of protective sleeve 82 initially confines proximal insertion end 30 of the catheter shaft 28 and also resists movement of the proximal insertion end of the catheter beyond the sleeve tip 88 of the protective sleeve 82 until after the proximal insertion end 30 of catheter shaft 28 and sleeve tip 88 have been inserted into the distal portion of the urethra. The catheter shaft 28 can be inserted through the urethra into the bladder following insertion of the sleeve tip 88 of the protective sleeve 82 into the distal portion of the urethra by movement of the proximal insertion end 30 of the catheter shaft 28 against the sleeve tip 88 of the protective sleeve 82 with sufficient force to cause the proximal end portion 100 of sleeve tip 88 to rupture. The structure of the rupturable sleeve tip 88 of protective sleeve 82 and the configuration of the rupturable proximal end portion 100 may vary, and can include, for example, one or more of the exemplary embodiments described above and illustrated in FIGS. 3-7A. Preferably, the end portion 100 of sleeve tip 88 comprises a slit, perforation or opening closed by at least one seal to initially confine the catheter proximal insertion end 30, which slit or opening can be ruptured by moving insertion end 30 against the end portion 100 of the sleeve tip 88 with sufficient force.

In any event, it is preferable that during use, the sleeve tip 88 and the catheter proximal insertion end 30 covered by the sleeve tip are inserted or advanced into the urethral opening 62 as illustrate in FIG. 14. The sleeve tip 88 is inserted until edge/stop surface 98 of the band of material 92 abuts the meatus M of the penis (or the urethral opening for females, not shown) which substantially prevents further insertion of the sleeve tip 88 and sleeve 82 into the urethral opening 62. As described above, the catheter proximal insertion end 30 is continued to be advanced with sufficient force to cause the end portion 100 of sleeve tip to rupture. The catheter proximal insertion end 30 is then advanced through the urethra and into the bladder.

Regardless of the structure of the proximal end 40, 71, 100 of the protective sleeve tip 36, 70, 88 or catheter shaft protective sleeve tip portion 54a which may conform to any of the previously described embodiments or even other similar or equivalent arrangements, the catheter may then pass through the urethra into the bladder free of any restraint from the protective sleeve tip 36, 70, 88 or the catheter shaft sleeve tip portion 54b, as illustrated in FIG. 9.

In other respects, at least the protective sleeve tip 36, 70, 88 may be formed of a material having antimicrobial particles although it may also be desirable for the entire vapor permeable sleeve 54, 72, 82 to be formed of a material containing antimicrobial particles. The antimicrobial particles may be selected from a group consisting of ionic silver, zinc, ceragenin CSA-13, nitrofurazone, tetracycline and minocycline. Additionally, it is believed desirable for the length of the protective sleeve tip 36, 70 or catheter shaft protective sleeve tip portion 54b or 88 to extend beyond the flange portion 60 of the introducer flange 56 or beyond band of material 74 or 92 by between about 10 mm and about 30 mm.

With regard to these dimensions, it is believed that having the protective sleeve tip 36, 70 or the catheter shaft protective sleeve tip portion 54b or 88 extend beyond the flange or band portion 74 or 92 by between about 10 mm and about 30 mm will be sufficient to fully traverse the distal urethra so the proximal insertion end 30 will not pick up pathogens once it has ruptured or otherwise passed through the proximal end 40, 71, 100 of the protective sleeve tip 36, 70, 88 or the catheter shaft protective sleeve tip portion as the catheter 26 is being inserted through the urethra into the bladder.

With regard to the thin, flexible material of the vapor permeable sleeve 54, 72, or 82 it may comprise a polyurethane or polyethylene film as previously described for the protective sleeve tip 36, 70. In still other respects, the vapor permeable sleeve may also comprise an elastomeric hydrogel film, may be selected from a group consisting of plasticized PVC and polypropylene, or may comprise a polyurethane polyethylene oxide block copolymer. Further, the vapor permeable sleeve may have a thickness within the range of about 10 to about 150 microns and, more preferably, about 13 to about 50 microns to facilitate no-touch gripping of the catheter.

In addition to the foregoing, the thin, flexible material of the vapor permeable sleeve 54, 72 or 82 may comprise a material that is inherently lubricious without swelling including fluorinated polymers (such as PTFE and PCTFE and short fluoro alkyl chains), polymers with suitably patterned surfaces which may exhibit lubricity due to their lower contact area, polymers that contain an alkyl amine or a zinc stearate processing aid, polymers used for bearing and moving surface applications which have high wear resistance (such as polyoxymethylene copolymers and Nylon polymers), and polymers containing low molecular weight functional silicone (such as silicone oil-added or copolymerized) and alkyl groups.

While the foregoing sets forth details of the present disclosure, it will be appreciated by those skilled in the art that the details herein given may be varied without departing from the true spirit and scope of the appended claims.

The invention claimed is:

1. A protective sleeve for a urinary catheter, comprising:
   a sleeve configured to extend over an outer surface of a urinary catheter shaft from a proximal insertion end of the catheter shaft to a distal end of the catheter shaft;
   a protective sleeve tip defining a proximal end portion of the sleeve;
   wherein the sleeve and protective sleeve tip are of a single unitary construction and the sleeve and protective sleeve tip are formed of the same thin, flexible film;

the protective sleeve tip having:
- a first pre-use configuration when the proximal insertion end of the urinary catheter is not within the protective sleeve tip wherein the protective sleeve tip is in a collapsed state, and
- a second configuration when the proximal insertion end of the urinary catheter is inserted into the protective sleeve tip, in the second configuration the protective sleeve tip being in an extended state that is configured to cover the proximal insertion end of the urinary catheter shaft and the thin, flexible film conforms to and is supported by the proximal insertion end of the urinary catheter for insertion of the protective sleeve tip into the urethral opening.

2. The protective sleeve of claim 1, wherein the protective sleeve tip has a rupturable proximal end.

3. The protective sleeve of claim 2, wherein the rupturable proximal end is configured to confine the proximal insertion end of the urinary catheter within the protective sleeve tip.

4. The protective sleeve of claim 2, wherein the rupturable proximal end of the protective sleeve tip is configured to rupture to allow advancement of the catheter through the remainder of the urethra.

5. The protective sleeve of claim 2, wherein the rupturable proximal end comprises a slit closed by at least one seal.

6. The protective sleeve of claim 2, wherein the rupturable proximal end comprises a perforation.

7. The protective sleeve of claim 6, wherein the perforation comprises two cross perforations.

8. The protective sleeve of claim 2, wherein the rupturable proximal end of the protective sleeve tip comprises a semi-cylindrical shape terminating in a single opening smaller than the diameter of the catheter shaft.

9. The protective sleeve of claim 2, wherein the rupturable proximal end of the protective sleeve tip comprises a semi-cylindrical shape terminating in three openings each smaller than the diameter of the catheter shaft.

10. The protective sleeve of claim 2, wherein the rupturable proximal end of the protective sleeve tip comprises a semi-cylindrical shape terminating in five openings each smaller than the diameter of the catheter shaft.

11. The protective sleeve of claim 2, wherein the rupturable proximal end of the protective sleeve tip comprises an inwardly curved shape terminating in a linear opening shorter in length than the diameter of the catheter shaft.

12. The protective sleeve of claim 2, wherein the rupturable proximal end of the protective sleeve tip comprises an hour glass shape terminating in a linear opening and a minimum hour glass spacing less than the diameter of the catheter shaft to confine the proximal insertion end of the catheter shaft.

13. The protective sleeve of claim 1 wherein the protective sleeve tip has an outer surface having a hydrated hydrophilic coating thereon facilitating insertion of the proximal end of the protective sleeve tip into the urethra.

14. The protective sleeve of claim 1 wherein the thin, flexible material from which the protective sleeve is formed is selected from a group consisting of polyurethane and polyethylene.

15. The protective sleeve of claim 1, wherein the protective sleeve tip has a thickness of between 0.5 mm and 35 mm.

16. A protective sleeve for a urinary catheter, comprising:
- a sleeve configured to extend over an outer surface of a urinary catheter shaft from a proximal insertion end of the catheter shaft to a distal end of the catheter shaft;
- a protective sleeve tip defining a proximal end portion of the sleeve;

wherein the sleeve and protective sleeve tip are of a single unitary construction and the sleeve and protective sleeve tip are formed of the same thin, flexible film;
the protective sleeve tip having:
- a first pre-use configuration when the proximal insertion end of the urinary catheter is not within the protective sleeve tip wherein the protective sleeve tip is in a collapsed state, and
- a second configuration when a proximal insertion end of a urinary catheter is inserted into the protective sleeve tip, in the second configuration the protective sleeve tip being in an extended state that is configured to cover the proximal insertion end of the urinary catheter shaft and the thin, flexible film conforms to and is supported by the proximal insertion end of the urinary catheter for insertion of the protective sleeve tip into the urethral opening;
- the protective sleeve tip has a tearable proximal end configured to confine the proximal insertion end of the urinary catheter within the protective sleeve tip; and the protective sleeve tip is configured to tear to allow advancement of the catheter through the remainder of the urethra.

17. The protective sleeve of claim 16 wherein the protective sleeve tip has an outer surface having a hydrated hydrophilic coating thereon facilitating insertion of the proximal end of the protective sleeve tip into the urethra.

18. The protective sleeve of claim 16 wherein the thin, flexible material from which the protective sleeve is formed is selected from a group consisting of polyurethane and polyethylene.

19. The protective sleeve of claim 16, wherein the protective sleeve tip has a thickness of between 0.5 mm and 35 mm.

* * * * *